United States Patent [19]

Burton et al.

[11] Patent Number: 4,938,760

[45] Date of Patent: Jul. 3, 1990

[54] FEMALE SUSPENSION PROCEDURE

[75] Inventors: John H. Burton, Minnetonka, Minn.; Reginald C. Bruskewitz, Madison, Wis.; Michael A. Mikulich, Shakopee; William D. Saville, Monticello, both of Minn.

[73] Assignee: American Medical Systems, Inc., Minnetonka, Minn.

[21] Appl. No.: 330,390

[22] Filed: Mar. 29, 1989

[51] Int. Cl.$^5$ ............................................. A61B 17/00
[52] U.S. Cl. .................................... 600/29; 128/898; 128/DIG. 25
[58] Field of Search ................... 128/334 R, 335, 344, 128/630, 774, DIG.25; 604/98–104; 600/29, 30

[56] References Cited

U.S. PATENT DOCUMENTS

| | | | |
|---|---|---|---|
| 2,075,508 | 3/1937 | Davidson | 128/335 |
| 3,527,223 | 9/1970 | Shein | 128/329 |
| 3,650,274 | 3/1972 | Edwards et al. | 128/335 |
| 3,664,345 | 5/1972 | Dabbs et al. | 128/335 |
| 3,845,772 | 11/1974 | Smith | 128/335 |
| 3,976,079 | 8/1976 | Samuels | 128/335 |
| 4,006,747 | 2/1977 | Kronenthal | 128/334 R |
| 4,139,006 | 2/1979 | Corey | 128/127 |
| 4,166,469 | 9/1979 | Littleford | 128/784 |
| 4,172,458 | 10/1979 | Pereyra | 128/340 |
| 4,291,698 | 9/1981 | Fuchs et al. | 128/335 |
| 4,669,478 | 6/1987 | Robertson | 128/630 |
| 4,705,040 | 11/1987 | Mueller et al. | 128/334 R |
| 4,741,330 | 5/1988 | Hayhurst | 128/92 YF |
| 4,790,328 | 12/1988 | Young | 128/748 |

OTHER PUBLICATIONS

Hadley et al., Urologic Clinics of North America, vol. 12, p. 291 (5/85).

Primary Examiner—Randall L. Green
Assistant Examiner—Gary Jackson
Attorney, Agent, or Firm—Peter C. Richardson; Lawrence C. Akers; Gezina Holtrust

[57] ABSTRACT

A method for suspending the urethrovesical junction in females comprises inserting sutures through a puncture or incision in the suprapubic abdominal area or through a puncture or incision in the vaginal wall, suspending the urethrovesical junction with the sutures, and anchoring the sutures with an anchoring means at an anchoring site. The anchoring means is a relatively rigid helix having an attaching means to attach the suture, or a pad adapted to be delivered with a delivery means to the anchoring site, or a flip anchor in substantial axial alignment with a placement means and adapted to be flipped from the axial alignment to an angled position, or an adjustable tissue anchor having a means for adjustably attaching the sutures.

5 Claims, 4 Drawing Sheets

FEMALE SUSPENSION PROCEDURE

BACKGROUND OF THE INVENTION

The invention relates to a method for suspending the female urethrovesical junction, also called bladder neck, with sutures and an anchoring means to anchor said sutures. The invention also relates to systems for positioning anchoring means in living tissue.

Stress incontinence is caused by increased abdominal pressure. One surgical method for treating this condition involves suspension of the bladder neck for repositioning in the correct fixed retropubic position such that there is no voiding of the bladder under stress and at the same time bladder outlet obstruction is avoided. Four relatively non-invasive surgical procedures for bladder neck suspension are described in Hadley et al., Urologic Clinics of North America, Vol. 12, No. 2, p. 291 (1985). In the original Pereyra method, a needle is passed from a suprapubic incision to an incision in the vagina near the bladder neck. Stainless steel suture wire is passed several times from the bladder neck to the suprapubic incision to suspend the bladder neck. The Cobb-Radge method inserts the needle from below through the vaginal incision. The Stamey procedure uses an endoscope to prevent the surgical needle from puncturing the bladder. Dacron vascular graft is used to anchor nylon suture in the periurethral tissue. Finally, in the Raz method the surgeon inserts his finger through the vaginal incision to guide the suspension needle and avoid penetration of the bladder by the needle. The sutures are anchored by threading through tissue of the vaginal wall and tissue in the suprapubic area.

A major problem encountered during surgical needle suspension procedures such as described above is the correct positioning of the bladder neck and the urethra such that the position of the bladder neck with respect to the bladder is high enough to avoid incontinence under stress while not too high to prevent proper bladder voiding.

The invention is an improvement over the prior art by providing for easy adjustment of the suspending sutures to lower or raise the bladder neck during surgery, and for readjustment to lower or raise the bladder neck, if necessary, after the patient has benefited from the suspension procedure. The invention also allows for more secure anchoring of the sutures without extensive tissue suturing to prevent lowering of the bladder neck over time. Furthermore, the invention reduces the amount of tissue dissection required to place the tissue anchors in proper position.

A system for positioning of anchoring means used during surgical procedures is described in U.S. Pat. No. 4,705,040 disclosing a hollow needle containing a retaining device attached to a filament. The retaining device after dislodging from the needle attaches to the interior wall of a body organ, and the filament is pulled to draw the device against the body wall. The filament is clamped outside the body to keep the organ in position.

U.S. Pat. No. 4,166,469 describes placement of a pacemaker within a patient through a sleeve which is positioned in the body through a needle or over a guide wire which enters the patient within a needle and remains after the needle is removed.

The above prior art devices are helpful in introducing objects into the body, but do not have the versatility of the systems of the invention described below.

SUMMARY OF THE INVENTION

According to the invention, the urethrovesical junction is suspended by inserting sutures through an incision in the suprapubic abdominal area or through an incision in the vaginal wall, suspending said urethrovesical junction with said sutures, and anchoring said sutures with at least one anchoring means at an anchoring site, wherein said anchoring means is: a relatively rigid helix having an attaching means to attach said suture, or a pad adapted to be delivered within a delivery means to said anchoring site, or a flip anchor in substantial axial alignment with a placement means and adapted to be flipped from said axial alignment to an angled position with respect to said placement means, or an adjustable tissue anchor having a means for adjustably attaching said sutures. In the context of the invention, incision is understood to include mere puncture by a needle.

The invention is also directed to a system for positioning an anchoring means in living tissue, which comprises an insertion means primarily defined along a longitudinal axis to fit in a surgical needle, and an anchoring means having a substantially axial channel reversibly surrounding said insertion means in substantially axial alignment with said longitudinal axis of said insertion means. Said anchoring means in one embodiment of the invention is adapted to be flipped from said axial alignment to an angled position. Conveniently, said insertion means is a surgical guide wire threaded through said substantially axial channel of said anchoring means.

The invention further includes an anchoring means for anchoring a suture in tissue, which comprises a housing, a substantially cylindrical means for receiving a suture, said cylindrical means contained within said housing, and an adjusting means in mechanical relationship with said cylindrical means such that on adjusting said adjusting means the length of said suture within the tissue can be regulated. In one embodiment said adjustment of the anchoring means is by rotation of said adjusting means. In a second embodiment, said cylindrical means is a rotating spool capable of being rotated through adjustment of said adjusting means.

The invention, finally, includes an anchoring means for anchoring a suture in tissue, which comprises a housing, a rotating spool contained within said housing for receiving a suture, a driving gear in reversible engagement with said rotating spool such that on engagement with said rotating spool, said spool may be rotated in one direction and on disengagement said spool may be rotated in the opposite direction, and an adjusting means in mechanical relationship with said driving gear such that on adjustment of said adjusting means the driving gear may be reversibly engaged with said rotating spool to regulate the length of said suture within the tissue.

Preferably, said adjusting means is adapted for external access to adjust said adjusting means by external means. It is understood that "external access" means access from outside the anchoring means, and, more specifically, from outside the body, e.g. by way of puncturing the skin or through a small incision (e.g. 2 to 4 mm) of the skin.

Generally, introduction of an anchoring means into the tissue can be by inserting a hollow needle carrying the anchoring means attached to a suture through the skin into the tissue, releasing the anchoring means from the hollow needle into the tissue and withdrawing the hollow needle.

Specific manners in which the anchoring means maybe employed for anchoring the suture in the tissue are described in more detail below.

DETAILED DESCRIPTION OF THE INVENTION

Figure 1:
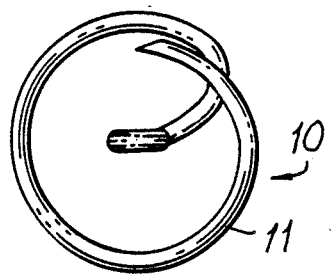
FIG. 1 is a top view of a relatively rigid helix of the invention.
Figure 2:
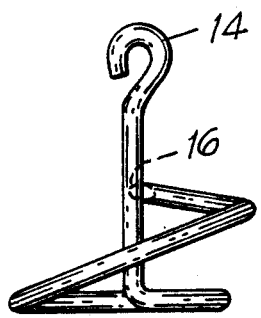
FIG. 2 is a side elevational view of the relatively rigid helix of FIG. 1.

FIGS. 1 and 2 show a relatively rigid helix 10 comprising one turn of a spiral 11 with the end of the spiral bent toward the center and then 90° upwards through the middle of the spiral to form shaft 12. The shaft 12 ends in an eye 14 for attaching a suture. The leading end 16 of the helix 10 is a sharp end to allow for screwing of the helix 10 into the body tissue.

The invention includes a rigid helix having more than one turn of the spiral. Conveniently, the end 16 is bend inwardly toward the shaft 12 for protection against erosion through adjacent critical organs such as the bladder and vagina. The eye 14 may be replaced by other suture attaching means such as a closed needle eye, or the shaft 12 may be hollow to enable swaging of a suture in the shaft in accordance with known hollow suture needles.

Figure 3:
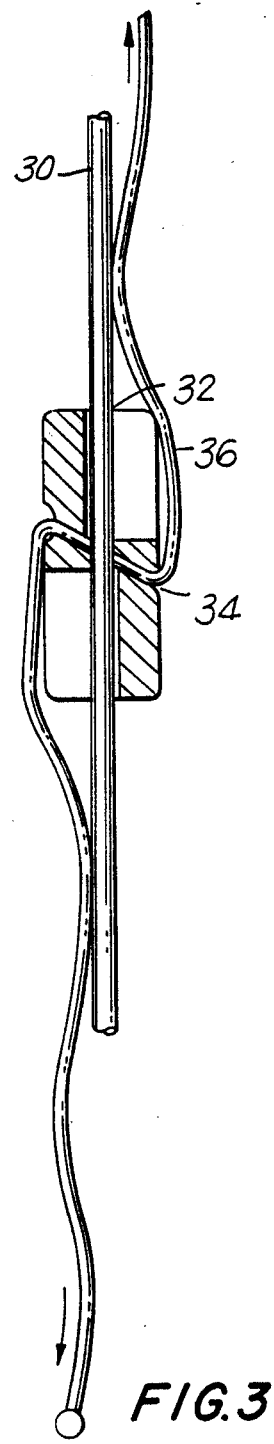
FIG. 3 is a sectional view of a flip anchor with a placement means.

FIG. 3 shows flip anchor 28 and placement means 30. The flip anchor 28 has an axial channel 32 which snugly fits around the placement means 30. The anchor 28 includes a radial channel 34 allowing for passage of a suture 36. The flip anchor 28 conveniently is in the shape of a flat rectangle. The placement means 30 is a surgical guide wire which may be placed in position by a needle, or a needle extension. On pulling at both ends of the suture 36, the anchor 28 flips and becomes positioned substantially at right angles to the means 30. In an alternative embodiment, the flip anchor may have a means for attachment to a tool which is capable of flipping the anchor. Once the anchor 28 is in the flipped position, the suture 36 may be pulled from the suprapubic end.

Figure 4:
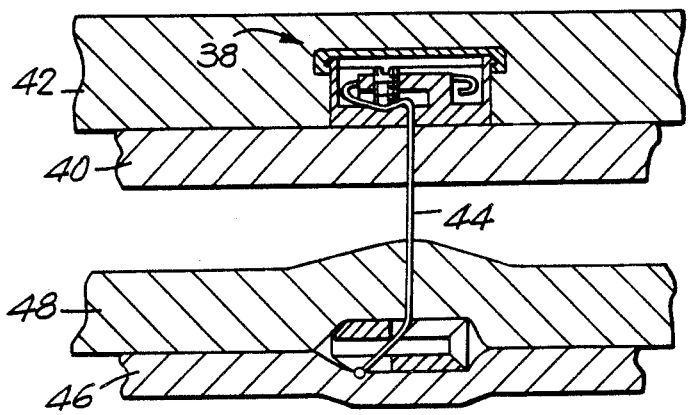
FIG. 4 is a sectional view of an adjustable tissue anchor placed in body tissue.

FIG. 4 shows an adjustable tissue anchor 38 placed between the rectus muscle 40 and subcutaneous tissue 42. Suture 44 extends between the tissue anchor 38 and anchoring means 46 placed between periurethral fascia 48 and vaginal wall 50. The anchoring means 46 may be properly positioned by introduction through a small incision of the vaginal wall. Alternatively, the anchoring means 46 may be introduced through a puncture of the vaginal wall by a needle. Thus, the flip anchor 28 of FIG. 3 may be positioned on a needle, as described above. Alternatively, a padlike tissue anchor may be inserted in a needle and pushed through the needle, for instance with an obtrator. The needle is subsequently withdrawn. The needle may have an extension known to have a certain length equal to the length between the desired position of the pad and the vaginal wall. This extension helps the surgeon in determining the distance which the needle has traveled through the vaginal wall, and thus the distance at which the anchoring means may be dropped.

Another method for positioning the anchoring means below the urethra between the vaginal wall and the periurethral fascia makes use of a solid needle having a sleeve. The needle punctures the vaginal wall when the proper position is attained, the needle is withdrawn leaving the sleeve behind in the tissue of the body. An anchoring means may then be inserted through the sleeve, and the sleeve withdrawn.

Figure 5:
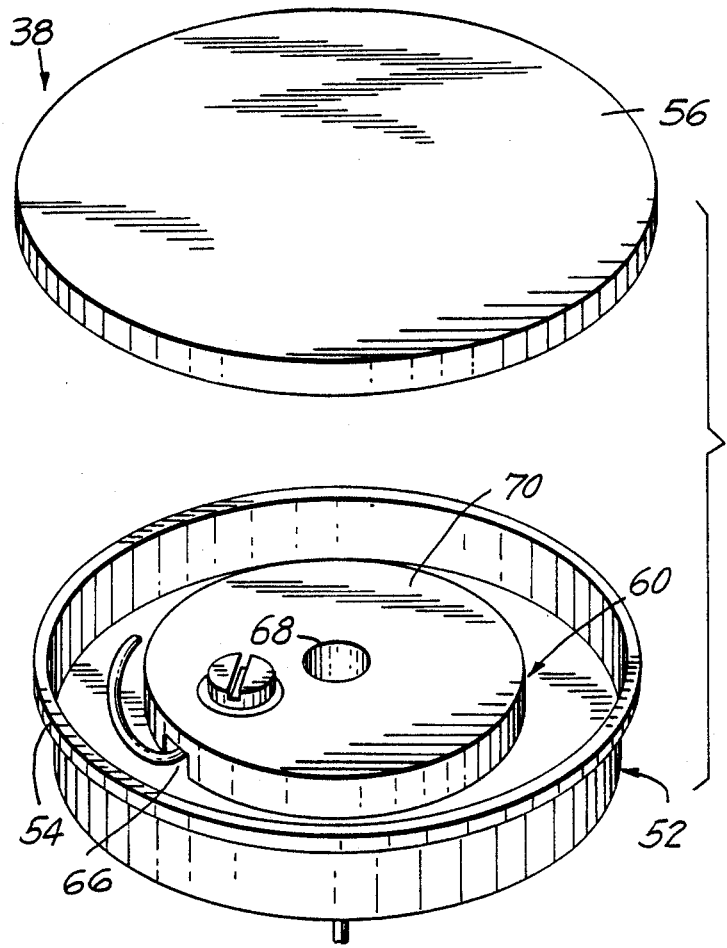
FIG. 5 is a perspective view of the externally adjustable tissue anchor of FIG. 4.

FIG. 5 shows the adjustable tissue anchor 38 of FIG. 4 in a perspective view. The tissue anchor 38 comprises substantially cylindrical anchor body 52 having snapping lip 54 to snap on cover lid 56. Anchor bottom 58 connects anchor body 52 with inner cylinder 60. Suture 62 is wrapped around inner cylinder 60, guided through channel 66 underneath suture-clamping screw 64 and through outer hole 68 which in FIG. 5 extends from the top 70 of the inner cylinder 66 through the anchor bottom 58. Suture 62 is clamped to the inner side of anchor bottom 58 by screw 64 when the anchor 38 is placed in the body. On removal of cover lid 56, screw 64 may be adjusted with a screwdriver. Thus, by screwing the screw 64 upwards, suture 62 is free for wrapping around inner cylinder 66 to shorten the length of the suture in the body, or the suture 62 is free for unwrapping from inner cylinder 66 to lengthen the suture in the body.

Figure 6:
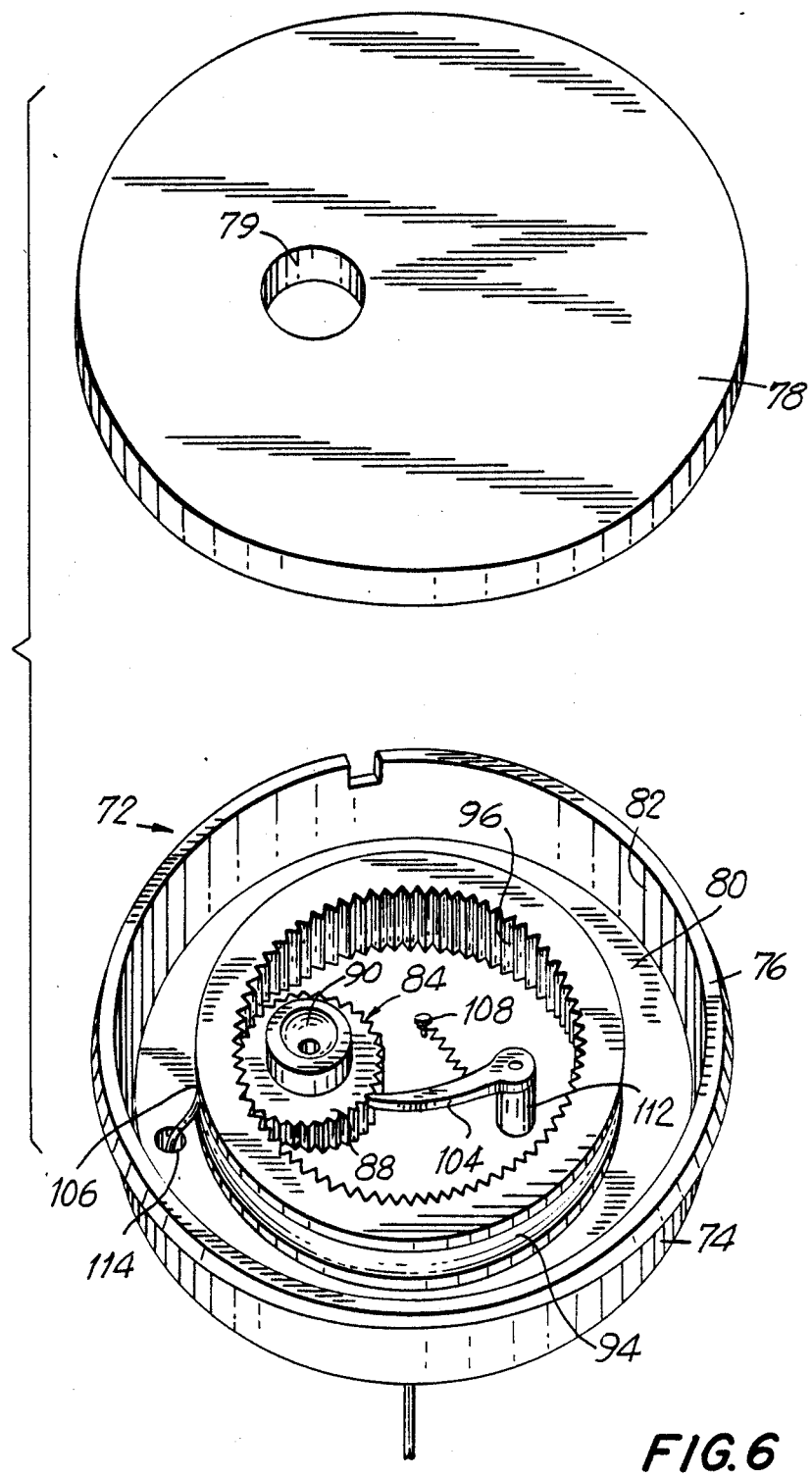
FIG. 6 is a perspective view of externally adjustable tissue anchor.
Figure 7:
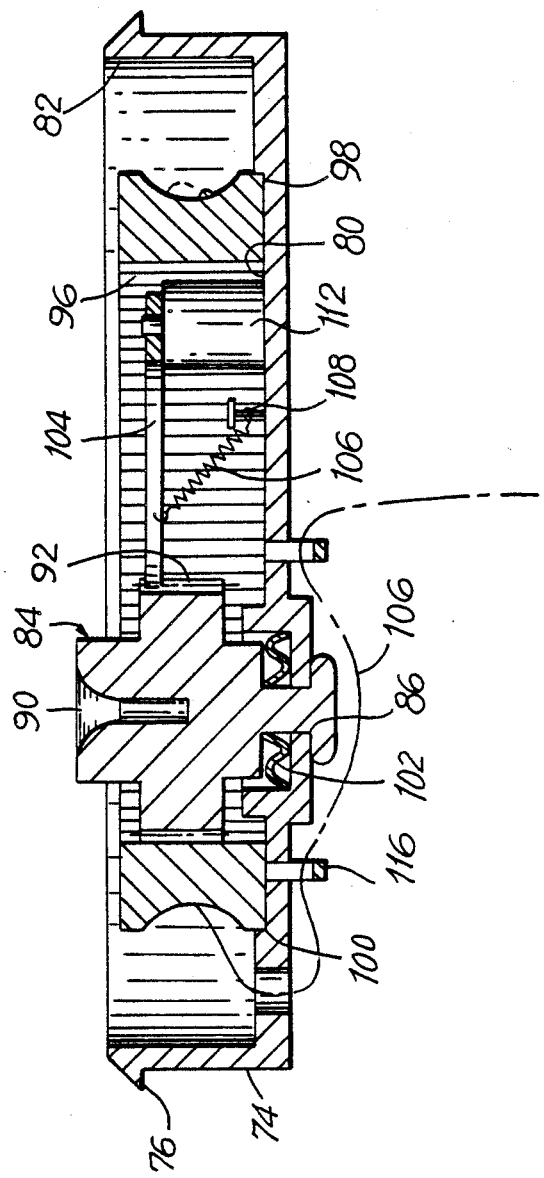
FIG. 7 is a sectional view of the tissue anchor of FIG. 6.

FIGS. 6 and 7 show an externally adjustable tissue anchor 72. The tissue anchor 72 comprises substantially cylindrical anchor body 74, snapping lip 76 to snap on cover lid 78 having access hole 79, bottom 80, tissue anchor wall 82 and rotating spool 94 on which suture 106 is wound. The spool 84 may be rotated with the aid of driving gear 84. Driving gear 84 is situated in opening 86 of the bottom 80. The driving gear 84 comprises funnel 88 leading to hex driving hole 90, and driving gear teeth 92. Rotating spool 94 has inside gear teeth 96 which are capable of engaging the driving gear teeth 92 of driving gear 84. The rotating spool 94 is locked in place between bottom edges 98 and 100 of the rotating spool bottom 80. Wave spring 102 is located under the driving gear 84. When the driving gear 84 is pushed downwards, e.g. by hand, the wave spring 102 allows the driving gear 84 to move down so disengaging ratcheting pawl 104. When the pawl 104 is disengaged, the rotating spool 94 can be rotated to release suture 106 from the spool 94. Rotation of the rotating spool 94 is with an external tool such as an Allen wrench, capable of puncturing through the skin into access hole 79 in cover lid 78 engaging the hex driving hole 90. On release of the driving gear 84, the wave spring 102 returns the driving gear 84 to its original position in engagement with ratcheting pawl 104 allowing for rotation of the rotating spool 94 for uptake of suture 106 on the spool 94. The ratcheting pawl 104 is attached to rotating spool bottom 80 through pawl spring 106 and spring post 108 and pivots on pawl pin 110 which is attached to pawl post 112. The pawl post 112 in turn is attached to bottom 80 or is part of bottom 80.

The suture 106 is spooled on rotating spool 94, channeled through hole 114 in bottom 80, and led through ridges or holes in extensions 116 and 118 at the bottom 80 to the center of the anchor 72.

The invention has been described with reference to preferred embodiments. Those skilled in the art will appreciate variations and modifications thereof. The following claims are intended to cover all modifications and variations falling within the spirit and scope of the invention.

We claim:

1. A method for suspending the urethrovesical junction with sutures which comprises inserting said sutures through an incision in the suprapubic abdominal area or through an incision in the vaginal wall, suspending said urethrovesical junction with said sutures, and anchoring said sutures with at least one anchoring means at an anchoring site, wherein said anchoring means is selected from the group consisting of:

a relatively rigid helix having an attaching means to attach said suture, or a pad adapted to be delivered within a delivery means to said anchoring site, or a flip anchor in substantial axial alignment with a placement means and adapted to be flipped from said axial alignment to an angled position with respect to said placement means, or an adjustable tissue anchor having a means for adjustably attaching said sutures.

2. A method according to claim 1 wherein said attaching means is a shaft located substantially centrally with respect to said helix 3. A method according to claim 1 wherein said delivery means is a needle and said pad is adapted to be delivered through the needle.

4. A method according to claim 1 wherein said placement means includes a guidewire reversibly attached to said flip anchor.

5. A method according to claim 4 wherein said guidewire is inserted through a hollow needle.

* * * * *